United States Patent
Young et al.

(10) Patent No.: US 9,170,231 B2
(45) Date of Patent: Oct. 27, 2015

(54) QUANTIFICATION AND CHARACTERIZATION OF ALLERGENS

(75) Inventors: Scott A. Young, Midland, MI (US); Barry W. Schafer, Cicero, IN (US); Krishna Kuppannan, Midland, MI (US); Samir Julka, Midland, MI (US); Dave R. Albers, Midland, MI (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 13/877,311

(22) PCT Filed: Aug. 22, 2011

(86) PCT No.: PCT/US2011/048645
§ 371 (c)(1),
(2), (4) Date: Jul. 8, 2013

(87) PCT Pub. No.: WO2012/044411
PCT Pub. Date: Apr. 5, 2012

(65) Prior Publication Data
US 2013/0280742 A1  Oct. 24, 2013

Related U.S. Application Data

(60) Provisional application No. 61/388,748, filed on Oct. 1, 2010.

(51) Int. Cl.
*G01N 27/62* (2006.01)
*G01N 30/72* (2006.01)
*G01N 30/78* (2006.01)
*G01N 30/46* (2006.01)
*G01N 30/88* (2006.01)
*G01N 30/74* (2006.01)

(52) U.S. Cl.
CPC ............ *G01N 27/62* (2013.01); *G01N 30/7233* (2013.01); *G01N 30/78* (2013.01); *G01N 30/463* (2013.01); *G01N 30/74* (2013.01); *G01N 2030/884* (2013.01)

(58) Field of Classification Search
None
See application file for complete search history.

(56) References Cited

PUBLICATIONS

Dugo et al., "Optimization of a Comprehensive Two-Dimensional Normal-Phase and Reversed-Phase Liquid Chromatography System", Journal of Chromatographic Science, vol. 44, Oct. 2006.*

Castro et al., "P urification and characterization of a small (7.3 kDa) putative lipid transfer protein from maize seeds", Journal of Chromatography B, 794 (2003) 109-114.*

Wang et al., "Analyses of macrolide antibiotic residues in eggs, raw milk and honey using both ultra-performance liquid chromatography/quadrupole time-of-flight mass spectrometry and high-performance liquid chromatography/tandem mass spectrometry." Rapid Communications in Mass Spectrometry, 2007, 21:3213-3222.*

Luoto, S., et al., "The identification of allergen proteins in sugar beet (*Beta vulgaris*) pollen causing occupational allergy in greenhouses," Clinical and Molecular Allergy, Aug. 11, 2008, vol. 6:7 (http://www.clinicalmolecularallergy.com/content/6/1/7).

Pastorello, E.A., et al., "The maize major allergen, which is responsible for food-induced allergic reactions, is a lipid transfer protein," Journal of Allergy Clinical Immunology, Jan. 27, 2000, vol. 106, pp. 744-751.

Porterfield, H.S., et al., "Effector activity of peanut allergens: A critical role for Ara h 2, Ara h 6, and their variants," Clinical Experimental Allergy, Jul. 31, 2009, vol. 39, pp. 1099-1108.

Svec, F., "Two-dimensional high-performance liquid chromatography," The Chemical Educator, Dec. 24, 1997, vol. 2, pp. 1-8.

Ong, E.K., et al., "Aeroallergens of plant origin: molecular basis and aerobiological significance," Aerobiologia, Dec. 31, 1995, vol. 11, pp. 219-229.

International Search Report for PCT/US2011/048645, mailed Apr. 9, 2012, 4 pages.

International Written Opinion for PCT/US2011/048645, mailed Apr. 9, 2012, 4 pages.

Monaci L., et al., "Development of a method for the quantification of whey allergen traces in mixed-fruit juices based on liquid chromatography with mass spectrometric detection," Journal of Chromatography, May 23, 2008, pp. 113-120, vol. 1192, No. 1.

Monaci L. et al., "Mass spectrometry-based 4 proteomics methods for analysis of food allergens," Trac. Trends in Analytical Chemistry, May 2009, pp. 584-591, vol. 28, No. 5.

Monaci et al., Development of a Method for the Quantification of Whey Allergen Traces in Mixed-fruit Based on Liquid Chromatography with Mass Spectrometric Detection, 113-120, May 2008, Journal of Chromatography A.†

Amigo-Benavent et al., Protein Quality, Antigenicity, and Antioxidant Activity of Soy-Based Foodstuffs, 6498-6505, Jul. 2008, Journal of Agricultural and Food Chemistry.†

Pastorello et al., The Maize Major Allergen, which is Responsible for Food-Induced Allergic Reactions, is a Lipid Transfer Protein, 744-751, Oct. 2000, Journal of Allergy and Clinical Immunology.†

\* cited by examiner
† cited by third party

*Primary Examiner* — Suzanne M Noakes
(74) *Attorney, Agent, or Firm* — Eric J. Kraus; Traskbritt, P.C.

(57) ABSTRACT

Embodiments of the invention include methods of determining the allergen content of a composition. Embodiments of the invention may include providing a composition comprising an allergen; at least partially purifying the allergen from the composition to form an extract; and determining the amount of allergen in the extract using liquid chromatography with ultraviolet and mass spectrometric detection.

12 Claims, 7 Drawing Sheets

SEQ ID NO:1

```
 1  AISCGQVASAIAPCISYARGQGSGPSAGCCS   31
32  GVRSLNNAARTTADRRAACNCLKNAAAGVSG   62
63  LNAGNAASIPSKCGVSIPYTISTSTDCSRVN   93
```

FIG. 4

FIG. 5 (page 1 of 2)

FIG. 5 (page 2 of 2)

FIG. 6

SEQUENCE LISTING

<160> NUMBER OF SEQ ID NOS: 3

<210> SEQ ID NO 1
<211> LENGTH: 93
<212> TYPE: PRT
<213> ORGANISM: Zea mays

<400> SEQUENCE: 1

Ala Ile Ser Cys Gly Gln Val Ala Ser Ala Ile Ala Pro Cys Ile Ser
1               5                   10                  15

Tyr Ala Arg Gly Gln Gly Ser Gly Pro Ser Ala Gly Cys Cys Ser Gly
            20                  25                  30

Val Arg Ser Leu Asn Asn Ala Ala Arg Thr Thr Ala Asp Arg Arg Ala
        35                  40                  45

Ala Cys Asn Cys Leu Lys Asn Ala Ala Gly Val Ser Gly Leu Asn
    50                  55                  60

Ala Gly Asn Ala Ala Ser Ile Pro Ser Lys Cys Gly Val Ser Ile Pro
65                  70                  75                  80

Tyr Thr Ile Ser Thr Ser Thr Asp Cys Ser Arg Val Asn
                85                  90

<210> SEQ ID NO 2
<211> LENGTH: 19
<212> TYPE: PRT
<213> ORGANISM: Zea mays

<400> SEQUENCE: 2

Ala Ile Ser Cys Gly Gln Val Ala Ser Ala Ile Ala Pro Cys Ile Ser
1               5                   10                  15

Tyr Ala Arg

<210> SEQ ID NO 3
<211> LENGTH: 19
<212> TYPE: PRT
<213> ORGANISM: Zea mays

<400> SEQUENCE: 3

Cys Gly Val Ser Ile Pro Tyr Thr Ile Ser Thr Ser Thr Asp Cys Ser
1               5                   10                  15

Arg Val Asn

QUANTIFICATION AND CHARACTERIZATION OF ALLERGENS

CROSS-REFERENCE TO RELATED APPLICATIONS

This application is a national phase entry under 35 U.S.C. §371 of International Patent Application PCT/US2011/048645, filed Aug. 22, 2011, designating the United States of America and published in English as International Patent Publication WO 2012/044411 on May 31, 2012, which claims the benefit under Article 8 of the Patent Cooperation Treaty and under 35 U.S.C. §119(e) to U.S. Provisional Patent Application Ser. No. 61/388,748, filed Oct. 1, 2010, for "QUANTIFICATION AND CHARACTERIZATION OF ALLERGENS," the disclosure of each of which is hereby incorporated herein by this reference in its entirety.

BACKGROUND

Lipid transfer proteins (LTPs) are low molecular weight proteins that were previously thought to play an important physiological role in transferring lipids between membranes in vitro. The proteins have been characterized in many plant species and are found in a variety of tissues and developmental stages[1]. They form a multigenic family and more than 50 amino acid sequences of plant LTPs are registered in the genome data banks. Two main families with different molecular masses have been isolated. One is composed by proteins with molecular mass of about 9 kDa and the other, by proteins with molecular mass of 7 kDa, referred to as LTP1 and LTP2, respectively. The LTP1 proteins are basic, presenting isoelectric points (pI) of between 9 and 10. Among the known sequences of LTP 1, all are characterized by having 90 to 95 amino acid residues, of which eight are cysteines conserved in similar positions along the primary structure. These cysteine residues are involved in intramolecular disulphide bridges that have been strictly conserved among LTP1s[1]. Furthermore, LTPs do not contain aromatic tryptophan or phenylalanine residues. Two well-conserved tyrosine residues are located toward the N- and C-termini of the polypeptide backbone. Proteins in both families are synthesized as precursor proteins and enter into the secretory pathway following a signal peptide cleavage. LTP1s from various plant species are localized at the cell wall in *Arabidopsis thaliana*[2], *Zea mays*[3], *Ricinus communis*[4], and *Vigna unguiculata*[5,6] seeds.

The functional role of LTPs in plants has been extensively debated. In *R. communis* kernels, a LTP isoform has been found inside an organelle, which was characterized as the glyoxosome. This LTP was shown to increase the activity of the acetyl-CoA oxidase enzyme in in vitro tests, suggesting involvement in βoxidation, possibly in the regulation of the catabolism of lipid storage[6]. In *Brassica oleracea* var. *italica*, LTP was found associated with the waxy surface of the leaves. The expression pattern suggests a role of the LTP in the transport of monomers of cutin[4]. In addition, abiotic stress factors such as drought, cold, and salt, have been described to upregulate members of the LTP family in some plant species[1,7-9]. Stabilization of membranes, cuticle deposition and/or changes in cell wall organization have been claimed as their putative roles in the responses to these stress factors[7,9,10]. In addition, LTPs have a potential role in plant growth and development, including embryogenesis[1], germination[11], and pollen-pistil interaction[12]. While the role of LTPs still remains obscure, the role in plant defense mechanisms against phytopathogens such as bacteria, fungi and viruses seems to be well established[1,13,14]. This has led to the classification of LTPs as pathogenesis-related (PR) proteins, which are included in the PR-14 family[14].

Furthermore, LTPs have recently been identified as plant food allergens. They have been identified as complete food allergens, in that they are capable of sensitizing, i.e., inducing specific IgE, as well as eliciting severe symptoms. LTPs appear to be a strong food allergen that are resistant to proteolytic attack and food processing. Stability allows the allergen to reach the gastrointestinal immune system in an immunogenic and allergenic conformation, allowing sensitization and induction of systemic symptoms. LTPs have been reported in fruits of Rosaceae[15,16,17] and Vitaceae[18] as well as in other plant species such as *Aspargus officinalis* and *B. oleracea* var. *capitata*[19,20]. Recently, a comprehensive study on maize allergens was conducted by Pastorello's group[21]. LTP was confirmed to be the major maize allergen by screening sera from 22 patients with systemic symptoms after maize ingestion with 19 (86%) of the patients recognizing the LTP 9 kDa protein. In a follow-up study, LTP was found to be an extremely stable protein, and maintains IgE-binding activity even after cooking at 100° C.[22]. In addition, maize LTP appears to also be resistant to gastrointestinal digestion[23]. Collectively, these properties enable members of the LTP class of proteins to be a strong food allergen that can cause severe reactions. Interestingly, maize LTP has been found to be a relevant allergen only in Southern Europe and also in a small group of patients from the U.S., suggesting that sensitization to LTP is relatively uncommon[24]. It is widely known that eight foods account for over 90% of food allergies, including peanuts, tree nuts, wheat, milk, eggs, crustaceans, soybean, and fish.

The role of LTP is, in many instances, still obscure because accurate absolute quantitation of the protein is difficult. Many of the previous studies are challenged by extensive sample preparation or inadequate, nonsensitive, and nonspecific in vitro bioassays. The commonly employed analytical methods for this purpose are based on immunological approaches. Although immunochemical methods generally are highly sensitive and compatible with high throughput, they suffer from limited specificity. Moreover, the development of antibodies for the target protein is a time-consuming process.

DISCLOSURE OF THE INVENTION

Embodiments of the invention include methods of determining the allergen content of a composition. Embodiments of the invention may include providing a composition comprising an allergen; at least partially purifying the allergen from the composition to form an extract; and determining the amount of allergen in the extract using liquid chromatography with ultraviolet and mass spectrometric detection.

DETAILED DESCRIPTION

Embodiments of the invention include methods of determining the allergen content of a composition. Embodiments of the invention may include providing a composition comprising an allergen; at least partially purifying the allergen from the composition to form an extract; and determining the amount of allergen in the extract using liquid chromatography with ultraviolet and mass spectrometric detection.

As used herein, an "allergen" is any substance that induces an allergic or hypersensitive response. In embodiments, the allergen may be a known allergen, e.g., substance that is known to produce an allergic or hypersensitive response in particular subjects. In embodiments, the allergen may be selected for analysis by the methods of the invention for the reason that it is a known allergen.

As used herein, an "allergic response" or "allergy" is a hypersensitive response or hypersensitivity caused by exposure to a particular allergen resulting in a marked increase in reactivity to that allergen upon subsequent exposure.

In embodiments of the invention, the liquid chromatography may be either one dimensional or two dimensional.

As used herein, "at least partially purifying the allergen from the composition to form an extract" means, in the case of solid compositions comprising the allergen, removing at least a portion of the allergen from the solid composition comprising a fluid composition to form an extract suitable for liquid chromatography with ultraviolet and mass spectrometric detection. In embodiments removing at least a portion of the allergen from the solid composition comprising a fluid composition may be carried out in any manner available to one of ordinary skill in the art. The extraction of proteins or other allergens from solid compositions is well known in the art and may be carried out in single or multi-step processes. Examples of techniques that may be used in the extraction of proteins or other allergens from solid compositions include, but are not limited to, maceration, liquefaction, lysis, sonication, freeze/thaw cycles, homogenization, filtration, electrophoresis, permeabilization, precipitation, denaturation, centrifugation, chromatography, differential solubilization, and filtration.

In the case of liquid compositions comprising the allergen, "at least partially purifying the allergen from the composition to form an extract," may be considered as being performed by the liquid chromatography step, which will separate the allergen away from one or more other components in the liquid.

In particular embodiments, the allergen may be a food allergen, latex allergen, and/or an aero-allergen. Examples of food allergens include, but are not limited to, food cereal crop, peanut, beans, peas, fruit, celery, sesame, tree nut, milk, egg, crustacean, fish, or potato allergens. Examples of food cereal crop allergens include, but are not limited to, soy, maize, and wheat allergens. In embodiments, the allergen may be maize lipid transfer protein.

As used herein, "aero-allergen" means any airborne substance that may cause an allergic response. Examples of aero-allergens include, but are not limited to, pollens and spores.

Embodiments of methods according to the invention may also comprise providing or isolating a source of purified allergen; and using the purified allergen to calibrate the equipment used to perform the liquid chromatography with ultraviolet and mass spectrometric detection.

In other embodiments, the composition comprising the allergen may comprise multiple isoforms or variants of an allergen. In further embodiments, methods according to the invention may be used to determine amounts of multiple different isoforms or variants of an allergen in a sample. In some embodiments, the determination of amounts of different isoforms or variants of an allergen may be determined with a single liquid chromatography step with an ultraviolet and/or mass spectrometric detection step.

LC-MS methods have recently been successfully developed to quantify and identify different biomarkers due to their high specificity, sensitivity, and accuracy in complex matrices[25,26]. The quantitation of proteins by LC-MS can be carried out either at the peptide level (signature peptides after proteolysis) or at the protein level (analysis of intact protein). The methodology of protein quantitation by analyzing a tryptic signature peptide using an isotopically labeled synthetic analogue as the internal standard has been described in detail[27]. However, the signature peptide approach may pose several challenges including, (a) a suitable peptide must be found whose sequence is specific only to the protein of interest[27], (b) the behavior of the internal standard may differ significantly compared to that of the intact protein prior to digestion, and (c) it relies on the tryptic digestion of the protein to be complete[28]. Quantitation of the intact protein by LC-UV/MS avoids the time-consuming and potentially problematic digestion step. In addition, different isoforms or variants may be resolved and quantified that would be missed by a signature peptide approach.

As described herein, LTP and analogues were purified and characterized from maize kernels. To achieve high specificity and sensitivity for the detection of LTP, an LC-UV/MS method was developed for rapid identification and quantification. This method was developed to demonstrate assay specificity, sensitivity, and quantitation accuracy in the comparison of 14 maize lines. The use of LC-UV/MS may result in minimized sample handling, reduced analysis time, and allow for accurate quantification of composition samples for the assessment of allergen levels.

EXAMPLES

The present invention is further described in the following examples, which are offered by way of illustration and are not intended to limit the invention in any manner.

Methods and Materials Used in Examples:

Materials:

Ammonium bicarbonate and MES buffer were purchased from Sigma (St. Louis, Mo.). HPLC grade isopropyl alcohol (IPA), trace metal grade ammonium hydroxide, sodium hydroxide, sodium chloride, glycerol, LC/MS grade trifluoroacetic acid (TFA), hydrogen chloride, dithioerythritol (DTE) and β-mercaptoethanol were purchased from Thermo Fisher Scientific (Pittsburgh, Pa.). HPLC-grade acetonitrile (ACN) and methanol was purchased from J.T. Baker (Phillipsburg, N.J.). STERIFLIP® disposable vacuum filtration system with 0.22 μM membrane filter was purchased from Millipore (Billerica, Mass.). SP Sepharose cation-exchange columns were purchased from GE Healthcare BioSciences (Piscataway, N.J.). Polypropylene auto sampler vial inserts were purchased from Agilent (Santa Clara, Calif.). CRITERION™ 4% to 20% Tris-HCl gels were purchased from Bio-Rad (Hercules, Calif.). Lys-C and trypsin were obtained from Roche Applied Sciences (Indianapolis, Ind.). For all analyses, MILLI-Q® (Millipore, Billerica, Mass.) deionized water was used.

Reference LTP Preparation: Purification of LTP from Non-Transgenic Maize Seed.

Extraction and isolation of the maize-derived LTP protein was performed as follows. Conventional maize kernels were ground to a fine powder with a ROBOT COUPE® grinder (Model #: RSI 2Y-1, Robot Coupe U.S.A., Inc.) containing an equal amount of dry ice. The dry ice was allowed to vent off overnight at −20° C. and the following day, 50 grams of powdered kernels were resuspended in 350 mL of 125 mM ammonium bicarbonate buffer. The pH of the mixture was adjusted to 8.0 with NaOH and the sample was heated at 72° C. for 2 hours with continuous mixing. The insoluble particulate was removed by centrifuging the sample at 37000 g for 5 minutes at 20° C. The resulting supernatant was filtered through P8 grade filter paper and the sample was digested with 5 mg of trypsin (Sigma Cat #T7168) overnight at 40° C. After proteolysis, the pH of the sample was lowered to 5.2 with HCl and the sample was further clarified by centrifugation at 30000 g for 15 minutes at 20° C. The resulting supernatant was filtered through a 0.45 μm filter and the sample was loaded onto a SP Sepharose column (5 mL/minute, mixed 50/50 with MILLI-Q® water) pre-equilibrated with 50 mM MES buffer, pH 5.5 (Buffer A). After sample loading, the column was washed extensively in Buffer A until the $A_{280}$ was reduced to baseline. The bound proteins were eluted with a linear gradient of Buffer A to Buffer B (Buffer A+0.5 M NaCl) and the collected fractions were examined by SDS-PAGE. The fractions containing the ~9 kDa LTP protein were combined and the protein concentration was determined by quantitative amino acid analysis. The pooled fractions were aliquoted into vials and stored at −80° C.

Sample Preparation: Isolation of LTP and LTP Variants from Maize Kernels.

Extraction of LTP from ground maize kernels was performed as previously reported with some modifications.[21] Briefly, ground maize kernels stored at −20° C. were thawed at room temperature in a dry box containing DRY-RITE™. Approximately 100 mg of ground maize kernels were weighed and 700 μL of 0.125 M ammonium bicarbonate buffer, pH 8.3, was added and mixed at 1,100 rpm for 2 hours at 22° C. using a THERMOMIXER®. The sample was clarified by centrifugation at 16100 g for 30 minutes and the resulting supernatant was transferred to a 1.5-mL microfuge tube. Prior to transferring an aliquot to an Autosampler vial, the extract was centrifuged again for 2 minutes at 16100 g.

SDS-PAGE Analysis and Protein Digestion.

To facilitate identification and characterization of the LTP sodium dodecyl sulfate-polyacrylamide gel electrophoresis (SDS-PAGE) was run with 4% to 20% Tris-HCl gels Bio-Rad (Hercules, Calif.). In brief, samples were diluted in Laemmli buffer with 5% β-mercaptoethanol. The resulting sample was centrifuged at 371 g for 45 seconds and then heated at 95° C. for 1.5 minutes. The separated proteins were detected with Coomassie Brilliant Blue R-250. Following separation and staining, the protein bands of interest were excised and incubated with trypsin or Lys-C at 37° C. overnight. The peptides were extracted from the gels with 50% ACN and 0.5% TFA in 25 mM ammonium bicarbonate buffer. Peptides remaining in the gel were then extracted with 70% ACN and 5% formic acid in 25 mM ammonium bicarbonate buffer. The extracts were pooled and dried in a VACUFUGE®. The dried peptides were reconstituted in 18 μL. The resulting proteolytic peptides were analyzed directly by mass spectrometry.

Mass Spectrometric Conditions for Characterization of LTP and Variants.

All mass spectra were acquired on an Agilent 6520 MICROMASS Q-ToF® mass spectrometer with an Agilent 1200SL Liquid Chromatography system. Chromatography was performed by gradient elution from ACQUITY® BEH130 C18 column (Waters, Milford, Mass.) at 50° C. with column dimensions of 100×2.1 mm and 1.7 μm particle size on an Agilent 1200SL system (Agilent, Santa Clara, Calif.). The column was equilibrated using 95% mobile phase A (0.1% (v/v) FA in water; MPA) and 5% mobile phase B (0.1% (v/v) FA in Acetonitrile; MPB) at a flow rate of 200 μL/minute. Injection volumes were varied between 5 μL and 20 μL. A linear gradient was employed from 5% MPB to 40% MPB over 17.2 minutes and from 40% MPB to 45% MPB over 1.7 minutes. The column was then re-equilibrated to initial conditions for 6 minutes.

Both UV (210 nm to 600 nm) and MS (200 amu to 1800 amu, 1 Hz) data were acquired. UV data was acquired using Agilent 1200SL Diode Array detector (Agilent, Santa Clara, Calif.). Positive-ion electrospray ionization (ESI) was performed on a 6520 QTOF mass spectrometer (Agilent, Santa Clara, Calif.) with a dual ESI ion source. Instrumental parameters for mass spectral acquisition were as follows: VCap was set at 3500 V, fragmentor at 145 V, skimmerl at 65 V, gas temperature at 350° C., gas flow at 8 L/minute, nebulizer at 310 kPa. During tandem MS experiments, targeted MS/MS with static exclusion ranges was employed. Peaks were isolated for tandem MS with a 9 amu width and a ramped collision energy of 3.6 V/100 Da+2 V was applied. All acquired data (MS and MS/MS) were processed manually.

Chromatographic and Mass Spectrometry Conditions for Characterization and Quantitation.

Chromatography was performed by gradient elution from ACQUITY® BEH300 C4 column (Waters, Milford, Mass.) at 70° C. with column dimensions of 100×2.1 mm and 1.7 μm particle size on an ACQUITY® UPLC system (Waters, Milford, Mass.). The column was equilibrated using 93% mobile phase A (0.1% (v/v) TFA in water; MPA) and 7% mobile phase B (0.1% (v/v) TFA in IPA; MPB) at a flow rate of 300 μL/minute. The samples were injected using a partial loop fill injection mode and 5 μL injection volumes. A linear gradient was employed from 7% MPB to 14.5% MPB over 15 minutes; MPB was then linearly ramped to 50.5% over 7 minutes. The column was then re-equilibrated to initial conditions for 5 minutes. Prior to injection of sample, the autosampler needle was washed with IPA (strong wash) and water (weak wash) to minimize sample carryover.

Both UV (215 nm, 10 Hz) and MS (700 amu to 2300 amu, 1 Hz) data were acquired. UV data was acquired using ACQUITY® TUV detector Waters (Milford, Mass.). Instrumental parameters for UV acquisition were as follows: Wavelength at 215 nm, sampling rate at 10 points/second, and time constant at 0.2 second. Positive-ion electrospray ionization (ESI) was performed on a MICROMASS Q-ToF® mass spectrometer (Waters, Milford, Mass.) with a lock-spray interface. Prior to MS inlet, a solution of 7% glycerol/68% water/25% acetonitrile was Tee'd-in to improve ionization efficiency in the presence of trifluoroacetic acid. Instrumental parameters for mass spectral acquisition were as follows: Capillary was set at 2850 V, sample cone at 35 V, extraction cone at 1.5 V, desolvation temperature at 410° C., source temperature at 100° C., low and high mass resolution at 5, desolvation gas at 600 L/hour, cone gas at 50 L/hour, MCP detector at 2350 V, scan time 0.9 second, interscan delay 0.1 second and collision energy at 10.

Method Development

Quantitation of LTP by ELISA has been the method of choice.[29] In the case of LTP from maize, due to the lack of a specific antibody, alternative approaches to quantitate LTP were considered. This led to the decision to develop a method for quantitative determination of maize LTP in the soluble fraction of maize extract by LC-UV/MS analyses. Absence of tryptophan residues in maize LTP prompted the use of the wavelength 215 nm. The wavelength of 215 nm was carefully chosen to minimize absorbance of the mobile phases (IPA and TFA), maximize analyte sensitivity, and maintain a constant baseline throughout the solvent gradient. The use of IPA and high temperature for reversed-phase protein separations has been previously shown to be critical to obtain good recovery and resolution[30]. To address the issue of specificity, the MS response was also monitored. To improve the mass spectrometer response in the presence of TFA, a pre-MS addition of a solution of glycerol in a water/acetonitrile mixture was performed. Enhanced signal-to-noise ratio and a shift to higher charge states were observed. The total ion current observed in the presence of glycerol/water/acetonitrile mixture was equivalent to the signal observed in the presence of formic acid in the mobile phase additive. Addition of glycerol has been previously shown to dramatically increase the ionization of protein and protein complexes during electrospray ionization.[31]

During method development, binding of reference LTP to glass vials was observed. This loss of LTP due to adsorption was observed when analyzing purified reference LTP. To minimize losses due to adsorption to Autosampler vials, polypropylene vial inserts were used for all analyses. In addition, during the LC-UV/MS analysis of reference LTP, bovine serum albumin at a concentration of 0.3 mg/mL was also included. Both the addition of bovine serum albumin and use of polypropylene vials were essential to maintaining linearity at lower concentrations.

Example 1

LTP MS Characterization

Figure 1:
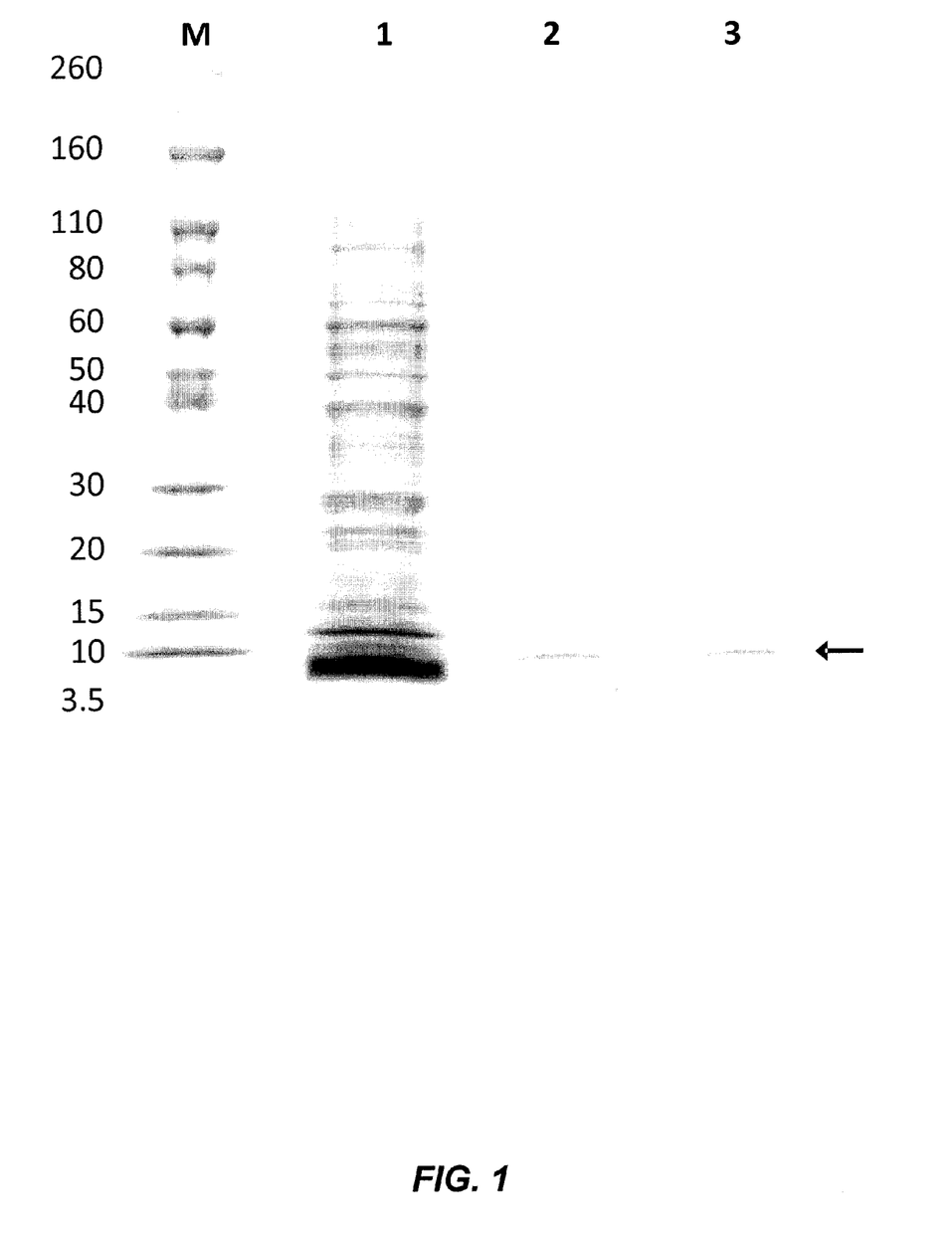
FIG. 1 depicts a sodium dodecyl sulfate-polyacrylamide gel electrophoresis (SDS-PAGE) analysis of endogenous LTP from maize seed following purification. M, molecular weight markers; lane 1 maize seed extract; lane 2, LTP fraction isolated from maize seed during LC-UV analysis; lane 3, LTP final reference. The arrow indicates the LTP band detected.
Figure 2:
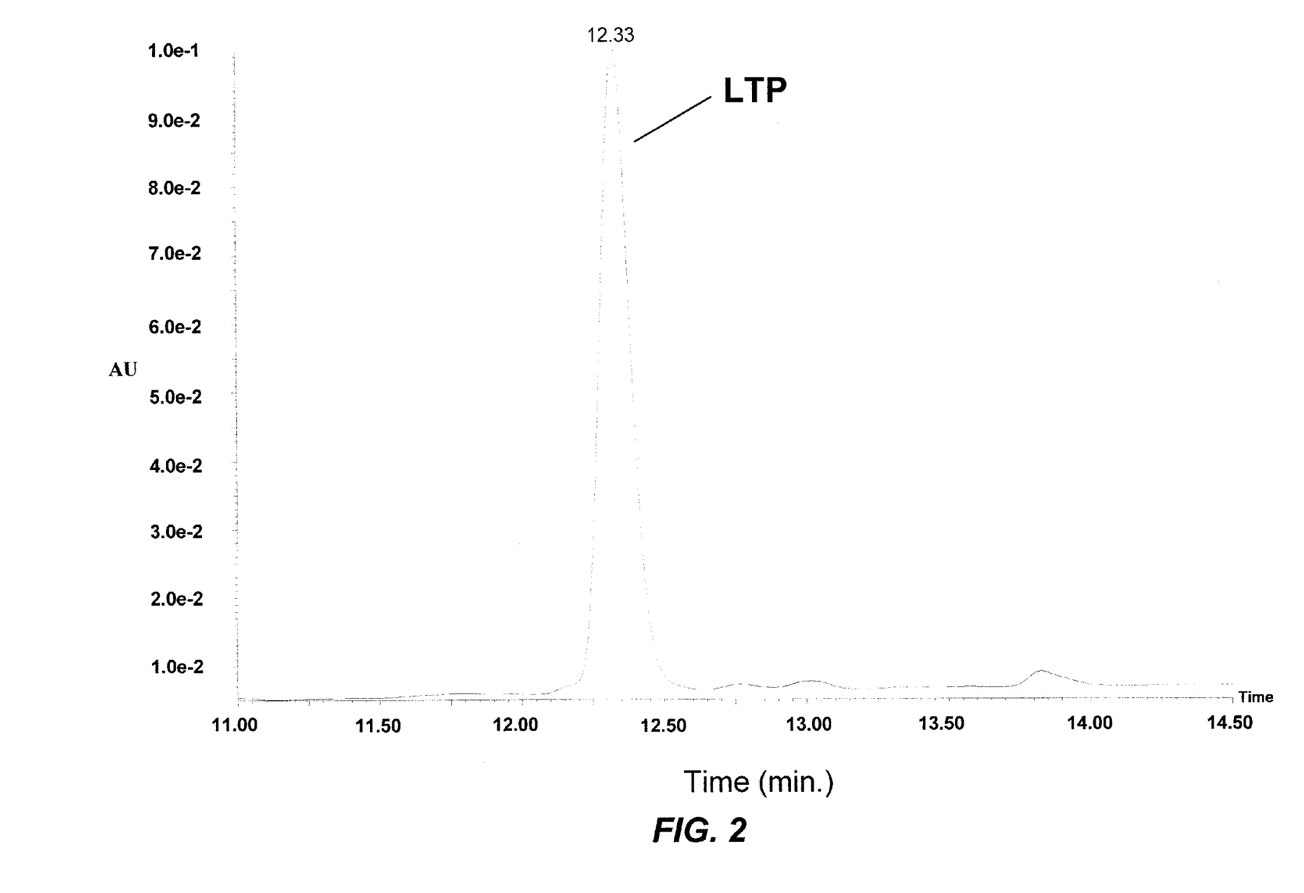
FIG. 2 depicts a LC-UV/MS (215 nm) chromatogram of intact MW of LTP reference standard.
Figure 3:
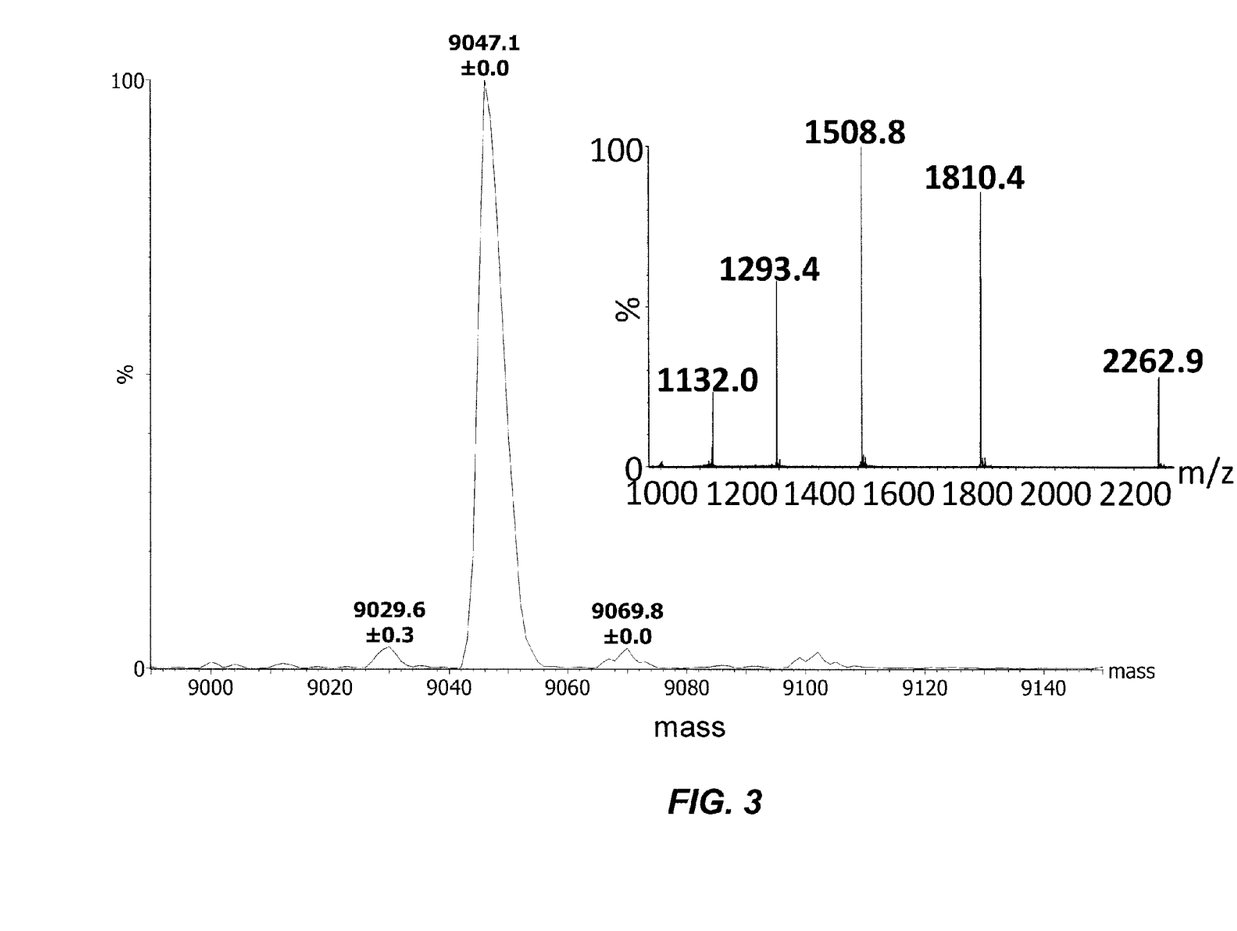
FIG. 3 depicts a deconvoluted mass spectrum of LTP reference (inset: multiple charge envelope mass spectrum).

Although lipid transfer proteins are the major allergens of maize, methods for their quantification have not been well established. Multiple molecular forms and isomers of LTP have been observed in many different tissues; as a result, analysis requires high sensitivity and selectivity because of the low concentration of the isoforms and structural similarities of these proteins. This led to the purification and characterization of LTP. Endogenous LTP in maize kernels was analyzed by SDS-PAGE after purification. As shown in FIG. 1, a protein band at approximately 9 kDa, representing the monomeric form of LTP was observed. FIGS. 2 and 3 depict the total ion chromatogram and the corresponding mass spectrum of the purified protein, respectively. The mass spectrum revealed the presence of a major component producing an $[M+H]^+$ ion at m/z 9047.1. This measured mass was within 0.01% of the theoretical precursor mass $[M+H]^+$ ion at m/z 9046.

Figure 4:
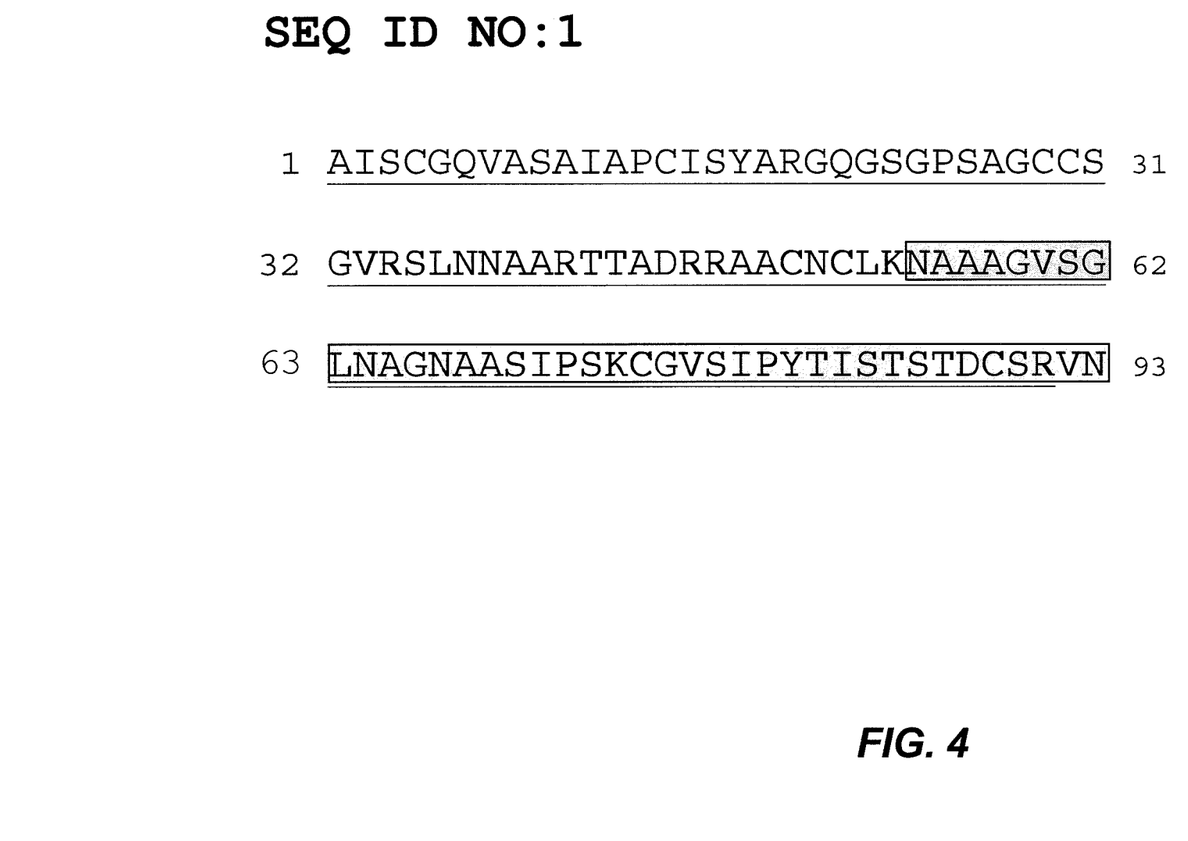
FIG. 4 depicts the deduced amino acid sequence of maize lipid transfer protein. The observed tryptic and Lys-C peptides using peptide mass fingerprinting are underlined and shaded, respectively.

The identity of the approximately 9 kDa protein band was further confirmed by peptide mass fingerprinting (PMF) after in-gel digestion using trypsin and Lys-C proteases. Compared with tryptic peptides and Lys-C peptides based on the amino acid sequence of maize LTP, full coverage of LTP was achieved (SEQ ID NO: 1) (FIG. 4). The N-terminal tryptic peptide, AISCGQVASAIAPCISYAR (SEQ ID NO: 2), and the Lys-C cleaved C-terminal peptide, CGVSIPYTISTST-DCSRVN (SEQ ID NO: 3), were further sequenced for confirmation by MS/MS using LC-MS/MS. Manual interpretation of the full scan MS and MS/MS spectra of all observed precursor charge states revealed the sequence. Every amino acid residue was confirmed at a minimum, by either a y or b ion series generated by fragment ions.

Example 2

Validation Experiments

The accuracy of the assay to measure LTP was evaluated by analyzing duplicate injections of maize kernel extracts spiked with reference LTP at eleven concentration levels (in the range from 4.1 to 147 µg/mL). A bracketed single point calibration was performed using reference LTP (84.7 µg/mL). To determine the LTP concentration in the unspiked extract, five injections of unspiked extract were performed. Assay accuracy (percent relative error, % RE) was calculated and is presented in Table 1 (*LTP concentrations are reported, both in terms of concentration in solution and corresponding concentration in seed.). Linearity of the method was also determined using the same data. A linearity curve was obtained by plotting the peak area of LTP versus concentration. A linear regression was used to obtain a linear equation over the range of 4.1 µg/mL to 147 µg/mL. For the linearity curve calculations, the equation was not forced through the origin.

TABLE 1

Multi-point accuracy for LTP spiked in a maize kernel extract.

| Expected LTP, µg/g* | Expected LTP, µg/mL* | Observed LTP, µg/mL | Accuracy (% RE) |
|---|---|---|---|
| 28.6 | 4.1 | 4.2 | 3.5 |
| 43.6 | 6.2 | 6.3 | 1.6 |
| 58.0 | 8.3 | 8.3 | 0.00 |
| 142 | 20.3 | 19.5 | −3.9 |
| 235 | 33.6 | 32.0 | −4.7 |
| 332 | 47.5 | 45.3 | −4.7 |
| 414 | 59.1 | 56.1 | −5.1 |
| 513 | 73.3 | 74.9 | 2.1 |
| 596 | 85.1 | 84.9 | −0.3 |
| 795 | 114 | 115 | 1.1 |
| 1030 | 147 | 144 | −1.7 |
|  |  | Average | −1.1 |

Precision of the assay to measure LTP was evaluated on each of four days by analyzing three replicate preparations of milled kernels (duplicate injections for each preparation) at three concentration levels (low, medium, and high). A sample set for each day was bracketed by a single-point reference LTP calibration standard (85 µg/mL). Assay intraday and interday precision (percent coefficient of variation, % CV) was calculated and are presented in Table 2.

TABLE 2

Intra- and inter-day precision for determination of LTP present in three different maize lines using single-point reference standard calibration.

| Day/Analyst/ Instrument | Statistic | Low | Medium | High | Pooled Statistic |
|---|---|---|---|---|---|
| 1/A/X | Mean (µg/g) | 51.2 | 238 | 472 | |
| | Precision (% CV) | 4.0 | 7.7 | 15.8 | 10.4 |
| | n | 3 | 3 | 3 | 9 |
| 2/A/X | Mean (µg/g) | 64.8 | 273 | 555 | |
| | Precision (% CV) | 6.7 | 1.8 | 8.4 | 6.3 |
| | n | 3 | 3 | 3 | 9 |
| 3/A/X | Mean (µg/g) | 51.3 | 233 | 480 | |
| | Precision (% CV) | 6.7 | 8.0 | 3.2 | 6.3 |
| | n | 3 | 3 | 3 | 9 |
| 4/B/Y | Mean (µg/g) | 53.7 | 227 | 472 | |
| | Precision (% CV) | 20.8 | 2.6 | 2.7 | 12.2 |
| | n | 3 | 3 | 3 | 9 |
| Overall | Mean (µg/g) | 55.3 | 243 | 495 | |
| | Precision (% CV) | 14.4 | 9.1 | 10.7 | 11.6 |
| | n | 12 | 12 | 12 | 36 |

Values have been rounded to show significant digits; statistical calculations have been done with full precision.

Due to the presence of endogenous LTP in all maize seed samples, selectivity of the assay was measured by intact molecular mass determination by ESI-LC/MS and analysis of the LC (LTP) fraction by SDS-PAGE. In addition, analyte carryover was evaluated by analyzing solvent blanks immediately following the highest standard sample. To determine the robustness of the method, the following parameters were investigated: extraction efficiency, column temperature, TFA concentration, and stability of reference LTP solution and maize kernel extracts.

Extraction efficiency of LTP from maize kernels was determined. Ground maize kernels from reference lines 3 and 13 were extracted by the above-detailed protocol for 1 hour, 2 hours, 5 hours or 17 hours. Extracted LTP concentration at these different time points was determined by LC-UV/MS analysis. In addition, the 2-hour extraction sample, after removal of 400 µL of supernatant, was further subjected to a second round of extraction for another 2 hours with further addition of 500 µL of ammonium bicarbonate buffer. Following extraction, the LTP concentration was determined by LC-UV/MS analysis and a correction was applied to account for LTP left over from the first round of extraction.

Effect of column temperature (65° C., 70° C. and 75° C.) and TFA concentration (0.09%, 0.1% and 0.11%) on chromatographic resolution and LTP quantitation was evaluated using ground maize kernel extracts. For determination of concentration, reference LTP was also analyzed under the same experimental conditions.

Stability of reference LTP and maize kernel extracts at room temperature and 4° C. was evaluated over a period of 48 hours. An aliquot of maize kernel extract and reference LTP were stored at 4° C. and room temperature for 48 hours. Response of both reference LTP and maize kernel extract was measured immediately after sample preparation. Following storage, the stability samples were analyzed by LC-UV/MS. Stability was evaluated by comparing the stored samples to freshly prepared reference LTP.

To characterize the LTP variants with retention times of 12.7 and 13.1 minutes, 20 mL of maize kernel extracts (reference line #5) were injected multiple times and fractions were collected manually. Collected fractions were pooled, evaporated in a CENTRIVAP® apparatus and subjected to SDS-PAGE. Protein bands were excised and subjected to Lys-C or tryptic digestion and peptides were extracted out of the gel. Extracted peptides were then analyzed by LC-MS/MS.

Figure 5:
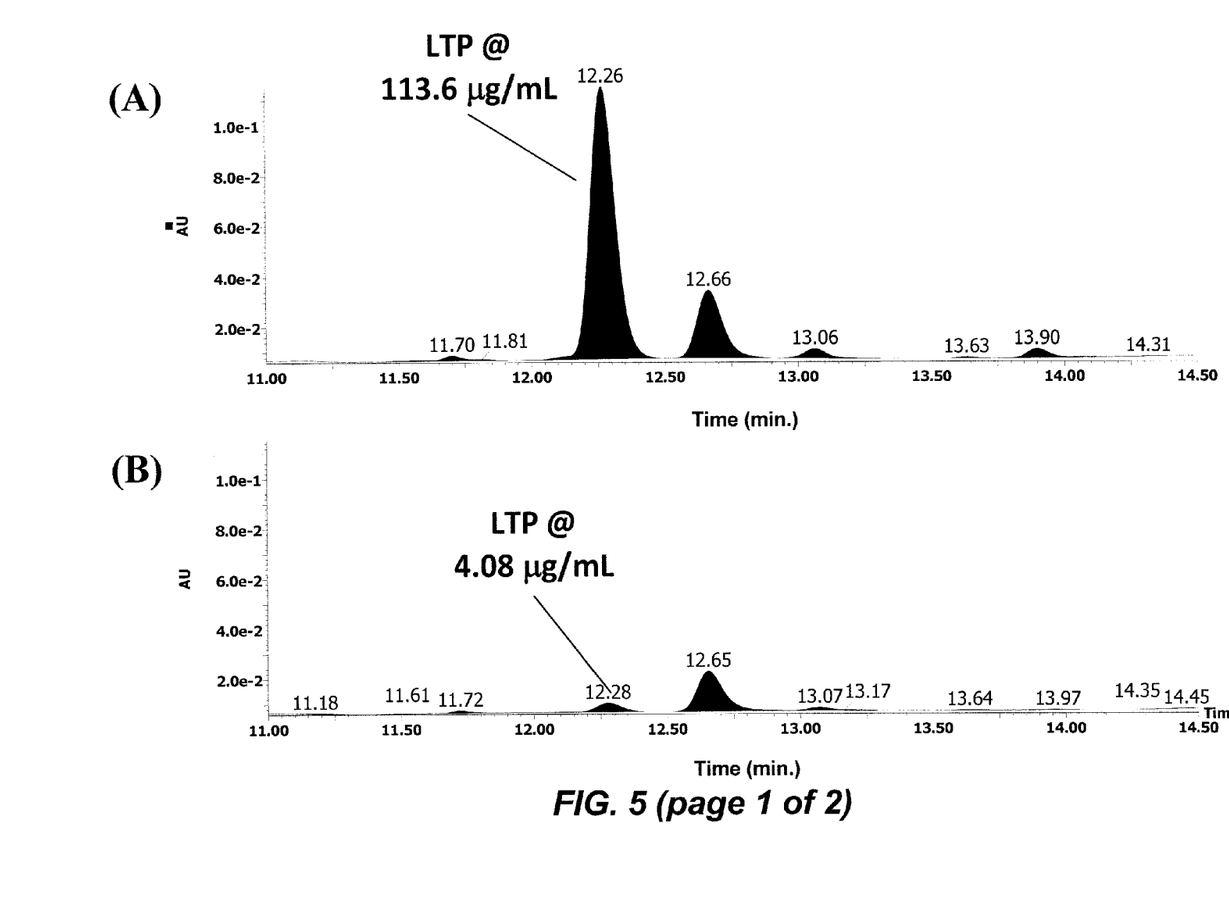
FIG. 5(A) depicts a LC-UV/MS (215 nm) chromatogram obtained from the analysis of maize kernel extract spiked with reference LTP with a total LTP concentration of 113.6 μg/mL.
FIG. 5(B) depicts a LC-UV/MS (215 nm) chromatogram obtained from the analysis of maize kernel extract spiked with reference LTP with a total LTP concentration of 4.08 μg/mL.
FIG. 5(C) depicts a typical standard curve for LTP determination over the range of 4.1 to 147 μg/mL.
Figure 6:
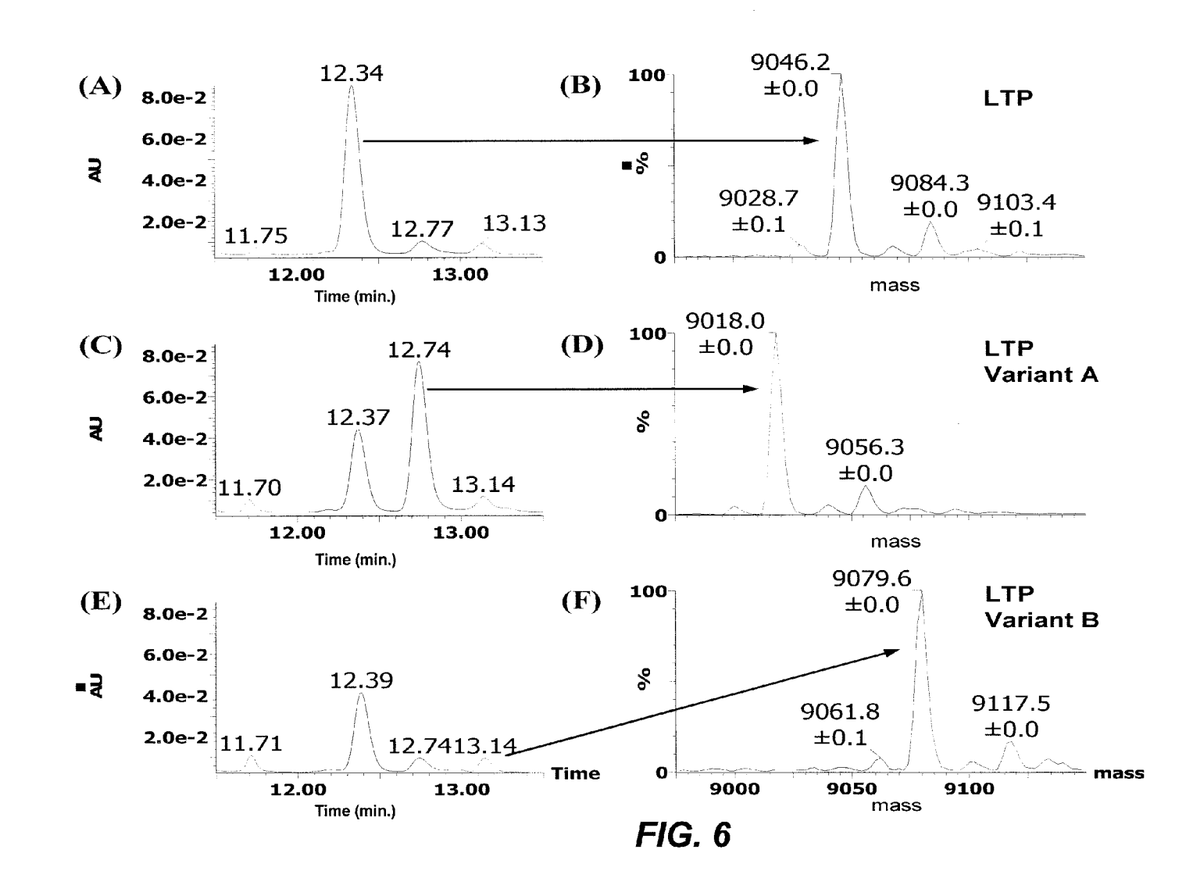
FIG. 6(A) depicts a UV (215 nm) chromatogram of maize kernel extracts from Line #13.
FIG. 6(B) depicts a deconvoluted mass spectrum of the components with the retention time of 12.34 minutes.
FIG. 6(C) depicts a UV (215 nm) chromatogram of maize kernel extracts from Line #5. Y-axis has been normalized to maize kernel line #13.
FIG. 6(D) depicts a deconvoluted mass spectrum of the components with the retention time of 12.74 minutes.
FIG. 6(E) depicts a UV (215 nm) chromatogram of maize kernel extracts from Line #5. Y-axis has been normalized to maize kernel line #4.
FIG. 6(F) depicts a deconvoluted mass spectrum of the components with the retention time of 13.14 minutes.

Aqueous extracts from kernels of certain lines of maize contain protein variants that are similar in mass and have similar retention characteristics on the reversed-phase column. The specificity of the method to resolve LTP from other proteins with similar reversed-phase retention characteristics can be inferred from FIG. 5. While the peak with a retention time of 12.3 minutes in FIG. 6 corresponds to maize LTP, the peak at 12.7 and 13.1 minutes corresponds to LTP variants A and B, respectively. Baseline resolution is obtained for the separation of these two proteins with a measured resolution of 1.6. The purity of the LTP peak is further illustrated in the SDS-PAGE shown in FIG. 1 (lane 2). Further characterization of the LTP variants A and B were conducted by collecting the LC fractions and subjecting them to in-solution proteolysis with trypsin or endoproteinase Lys-C and then analyzing the peptides by LC-MS/MS. Peptide mass fingerprinting and tandem MS data revealed that LTP variant A had a single amino acid polymorphism at position 34 (arginine to lysine). This was also corroborated by the 28 amu difference observed between LTP and LTP variant-A by intact molecular weight measurements (FIG. 6, Panels B and D). Based on partial peptide mass fingerprinting and intact molecular weight analysis, the exact site(s) of modification (+33 amu) for LTP variant B could not be confirmed. These results further illustrate the specificity of the developed LC-UV/MS method. Column temperature was a critical factor in obtaining the resolution of these two components. At temperatures of 60° C. and 90° C., the resolution between these two pairs of components was inadequate.

The presence of endogenous LTP in the maize kernels complicated the preparation of LTP reference standard samples for the overall validation of the assay. Consequently, to develop a validation study, the LTP concentration in non-spiked maize kernel extract was first determined by using the LTP reference standard. The endogenous LTP level present in the maize kernel line used for linearity and accuracy studies was found to be 58 µg/g. Linearity and accuracy of the assay was measured at 11 concentrations using maize kernel extract by spiking with reference LTP or diluting with ammonium bicarbonate buffer. The assay was observed to be linear over the range of 4.1 to 147 µg/mL for LTP in maize kernel extract (FIG. 5) with an $R^2$ value of 0.999. This concentration range corresponds to 28.6 to 1030 µg/g of LTP in maize kernel. The assay accuracy range (% RE) was 0% to 5.1% with recoveries in the range of 94.9% to 103% (Table 1). A signal-to-noise response of 215 was observed at the lowest measured concentration of LTP, 4.1 µg/mL.

To determine the linearity of the method, a serial dilution of the reference LTP in bovine serum albumin was performed. Though a linear response with a $R^2$ value of 0.999 was obtained, a rapid decrease of the response factor (area/concentration) was observed at LTP concentrations less than 44.2 µg/mL. This decrease was not observed when endogenous LTP in maize kernel extract was serially diluted with buffer down to a LTP concentration of 10.4 µg/mL. These observations could be indicative of a loss of LTP due to adsorption in the absence of matrix components.

The validation results for intraday and interday precision are presented in Table 2. Precision was measured by the use of three different maize kernel lines that were previously determined to have low, medium and high levels of LTP. Intermediate precision was also evaluated by the use of two analysts, two column lots, and two different LC systems. The precision range (% CV) was 9.1% to 14.4% with a pooled relative standard deviation of 11.6% over all the samples in this four-day period. Absolute carryover present in a blank sample that followed the high LTP maize kernel line was found to be approximately 0.6%. This translates to a LTP concentration of 6 µg/g in maize kernel. To further mitigate any carryover effects, solvent blanks were placed throughout the set to separate samples of analytical interest.

To determine the extraction efficiency, extracted LTP concentrations were measured after first and second extraction steps. A correction factor was applied to the LTP extracted after the second extraction step. After this correction, the concentration of LTP extracted in the first and second extraction steps were 32.1 and 1.61 µg/mL from reference line 3 and 88.2 and 8.75 µg/mL from reference line 13, respectively. The extraction efficiency in the first step is between 91% and 95%. Effect of time of extraction efficiency was also determined for reference lines 3 and 13 at 1 hour, 2 hours, 5 hours and 17 hours. For reference line 3, the LTP concentrations were 204, 225, 241 and 220 µg/g, respectively. For reference line 13, the LTP concentrations were 526, 619, 658 and 648 µg/g, respectively. Collectively, for both reference lines, the extraction efficiency at 2 hours is 94% of the efficiency observed at 5 hours.

loss of 1.91% and 4.75% was observed for the reference LTP in solution after 48 hours at 4° C. and room temperature, respectively. A loss of 8.3% and 11.5% was observed for the LTP in kernel extract after 48 hours at 4° C. and room temperature, respectively. To account for these losses, though the loss is within the precision of the assay, reference standard LTP was analyzed at the beginning, middle and end of each sample set.

Example 3

Analysis of LTP in Maize Lines

Fourteen different maize seed lines were prepared in triplicate as described. Duplicate injections of each preparation were subjected to LC-UV/MS analyses. The analysis was bracketed by a single-point LTP reference standard as the calibrant. The calibrant was also interspersed during the analysis of the reference lines. The response factor from reference LTP was used to determine the level of LTP and the two variants (a and b) at retention times of 12.7 and 13.1 minutes, respectively. The results are presented in Table 3.

TABLE 3

Determination of LTP and variant LTPA and LTPB from different maize lines.

| Line # | Line Name | LTP Concentration, µg/g | Precision (% CV) | LTP Variant A Concentration, µg/g | Precision (% CV) | LTP Variant B Concentration, µg/g | Precision (% CV) | Combined µg/g |
|---|---|---|---|---|---|---|---|---|
| 1 | CROPLAN 691 | 575 | 5.1 | 44 | 12.0 | 42.4 | 3.5 | 661 |
| 2 | DEKALB DKC62-30 | 218 | 5.2 | 345 | 4.8 | 44.6 | 8.1 | 607 |
| 3 | DEKALB DKC63-43 | 203 | 1.4 | 346 | 0.8 | 49.2 | 4.4 | 598 |
| 4 | LG 2597 | 304 | 3.3 | 49 | 12.9 | 51.6 | 15.5 | 405 |
| 5 | LG2615CL | 286 | 5.6 | 528 | 4.5 | 47.4 | 11.7 | 861 |
| 6 | PIONEER 32T16 | 466 | 10.0 | 31.2 | 30.1 | 20.5 | 11.5 | 518 |
| 7 | MIDLAND PHILLIPS 7B15P | 58.4 | 3.0 | 261 | 3.0 | 22.0 | 7.5 | 341 |
| 8 | NORTHRUP KING NK72-G8 | 74.3 | 3.4 | 319 | 5.0 | 38.2 | 4.5 | 432 |
| 9 | LG2620 | 512 | 9.4 | 56.9 | 15.4 | 38.7 | 12.8 | 608 |
| 10 | PIONEER 33T56 | 422 | 2.6 | 228 | 1.8 | 42.0 | 3.6 | 692 |
| 11 | MYCOGEN 2M796 | 126 | 14.5 | 503 | 9.9 | 25.3 | 25.7 | 654 |
| 12 | BURRUS645 | 72.3 | 15.3 | 284 | 5.6 | 20.3 | 20.2 | 377 |
| 13 | MYCOGEN 2M746-1 | 678 | 5.6 | 59.7 | 10.4 | 43.0 | 10.6 | 781 |
| 14 | MYCOGEN 2M746-2 | 516 | 12.7 | 42.0 | 32.3 | 27.4 | 23.2 | 586 |

Values have been rounded to show significant digits; statistical calculations have been done with full precision. % CV reported is based on µg/g.

Variation of column temperature and its effect on LTP concentration determination was evaluated. At column temperatures of 65° C., 70° C. and 75° C., the concentration of LTP was determined to be 44.7, 48.1 and 47.2 µg/mL, respectively. Upon variation, the TFA concentrations of 0.09%, 0.1% and 0.11% in the mobile phases A and B, determined LTP concentrations were 46.1, 43.8 and 47.1 µg/mL. The deviations observed here due to variation in column temperature and TFA concentrations are within the % RSD of the method.

Analyte stability of reference LTP in solution and LTP in kernel extract at 4° C. and room temperature was evaluated. A The level of LTP and its variants present in 14 maize kernel lines of interest was determined using the assay developed. The concentration of LTP and, variants A and B in the 14 lines varied between 58 µg/g and 678 µg/g, 31 µg/g and 528 µg/g, and 21 µg/g and 52 µg/g, respectively (Table 3). The expression level of LTP has been previously shown to be dependent on the tissue being analyzed and the stage of development of the tissue[3]. This study shows that the varying levels of LTP in maize kernels may be dependent on the genetic background or growing conditions of the individual maize lines. The precision (% CV) obtained for the analysis of the 14 maize lines is consistent with the precision of the assay determined during the validation studies. These results indicate that the LTP levels can be reproducibly measured using the assay method.

Example 4

Analysis of Allergen-Containing Compositions

Extracts of allergens from food cereal crops, peanuts, tree nuts, milk, eggs, crustaceans, fish, or potatoes, as well as reference standards for each allergen, are obtained. Duplicate injections of each extract are subjected to LC-UV/MS analyses. The analysis is bracketed by a single-point reference standard as the calibrant. The calibrant was also interspersed during the analysis of the reference lines. The response factor from reference standard was used to determine the level of allergen and variants thereof. The precision (% CV) obtained for the analysis of the different extracts is consistent with the precision of the assay determined during the validation studies. These results indicate that allergen levels can be reproducibly measured using the assay method.

While this invention has been described in certain embodiments, the present invention can be further modified within the spirit and scope of this disclosure. This application is, therefore, intended to cover any variations, uses, or adaptations of the invention using its general principles. Further, this application is intended to cover such departures from the present disclosure as come within known or customary practice in the art to which this invention pertains and which fall within the limits of the appended claims.

REFERENCES

1. Kader J.-C. *Annual Review of Plant Physiology and Plant Molecular Biology* 1996, 47:627-654.
2. Thoma S. L., Y. Kaneko, and C. Somerville. *Plant J.* 1993, 3:427-37.
3. Sossountzov L., L. Ruiz-Avila, F. Vignols, A. Jolliot, V. Arondel, F. Tchang, M. Grosbois, F. Guerbette, E. Miginiac, M. Delseny, P. Puigdomenech, and J.-C. Kader. *The Plant Cell*, 1991, 3:923-933.
4. Pyee J., H. Yu, and P. E. Kolattukudy. *Arch. Biochem. Biophys.* 1994, 311:460-468.
5. Carvalho A. O., C. E. S. Teodoro, M. Da Cunha, A. L. Okorokova-Facanha, L. A. Okorokov, K. V. S. Fernandes, and V. M. Gomes. *Physiol. Plant* 2004, 122:328-336.
6. Tsuboi S., T. Osafune, R. Tsugeki, M. Nishimura, and M. Yamada. *J. Biochem.* 1992, 111:500-508.
7. Kader J. C. *Trends Plant Sci.* 1997, 2:66-70.
8. Gaudet D., A. Laroche, M. Frick, R. Huel, and B. Puchalski. *Physiol. Plant.* 2003, 117:195-205.
9. Bubier J. and M. Schlappi. *Plant Cell Environ.* 2004, 27:929-936.
10. Douliez J., T. Michon, K. Elmorjani, and D. Marion. *J. Cereal Sci.* 2000, 32:1-20.
11. Eklund D. M. and J. Edqvist. *Plant Physiol.* 2003, 132:1249-1259.
12. Park S. Y., G. Y. Jauh, J. C. Mollet, K. J. Eckard, E. A. Nothnagel, L. L. Walling, and E. M. Lord. *Plant Cell* 2000, 12:151-164.
13. Garcia-Olmedo F., A. Molina, A. Segura, and M. Moreno. *Trends Microbiol.* 1995, 3:72-74.
14. van Loon L. and E. van Strien. *Physiol. Mol. Plant Pathol.* 1999, 55:514-519.
15. Diaz-Perales A., G. Garcia-Casado, R. Sanchez-Monge, F. J. Garcia-Salles, D. Barber, and G. Salcedo. *Clin. Exp. All.* 2002, 32:87-92.
16. Pastorello E. A., L. Farioli, V. Pravettoni, C. Ortolani, M. Ispano, M. Monza, C. Baroglio, E. Scibola, R. Ansaloni, C. Incorvaia, and A. Conti. *J. Allergy Clin. Immunol.* 1999, 103:520-526.
17. Pastorello E. A., L. Farioli, V. Pravettoni, M. G. Giuffrida, C. Ortolani, D. Fortunato, C. Trambaioli, E. Scibola, A. M. Calamari, A. M. Robino, and A. Conti. *J. Chrom. B. Biomed. Sci. Appl.* 2001, 756:95-103.
18. Pastorello E. A., L. Farioli, V. Pravettoni, C. Ortolani, D. Fortunato, M. G. Giuffrida, L. Perono Garoffo, A. M. Calamari, O. Brenna, and A. Conti. *J. Allergy Clin. Immunol.* 2003, 111:350-359.
19. Diaz-Perales A., A. I. Tabar, R. Sanchez-Monge, B. E. Garcia, B. Gomez, D. Barber, and G. Salcedo. *J. Allergy Clin. Immunol.* 2002, 110:790-796.
20. Palacin A., J. Cumplido, J. Figueroa, O. Ahrazem, R. Sanchez-Monge, T. Carrillo, G. Salcedo, and C. Blanco. *J. Allergy Clin. Immunol.* 2006, 117:1423-1429.
21. Pastorello E. A., L. Farioli, V. Pravettoni, M. Ispano, E. Scibola, C. Trambaioli, M. G. Giuffrida, R. Ansaloni, J. Godovac-Zimmermann, A. Conti, D. Fortunato, and C. Ortolani. *J Allergy Clin. Immunol.* 2000, 106:744-751.
22. Pastorello E. A., C. Pompei, V. Pravettoni, L. Farioli, A. M. Calamari, J. Scibilia, A. M. Robino, A. Conti, S. Iametti, D. Fortunato, S. Bonomi, and C. Ortolani. *J. Allergy Clin. Immunol.* 2003, 112:775-783.
23. Maleki S. J. *Curr. Opin. Allergy Clin. Immunol.* 2004, 4:241-245.
24. Nakajima O., R. Teshima, K. Takagi, H. Okunuki, and J. Sawada. *Regul. Toxicol. Pharmacol.* 2007, 47:90-95.
25. Ji Q. C., R. Rodila, E. M. Gage, and T. A. El-Shourbagy. *Anal. Chem.* 2003, 75:7008-7014.
26. Czerwenka C., I. Maier, N. Potocnik, F. Pittner, and W. Lindner *Anal. Chem.* 2007, 79:5165-5172.
27. Kirkpatrick D. S., S. A. Gerber, and S. P. Gygi. *Methods* 2005, 35:265-273.
28. Barnidge D. R., G. D. Hall, J. L. Stocker, and D. C. Muddiman. *Proteome Res.* 2004, 3:658-661.
29. Borges J. P., A. Jauneau, C. Brule, R. Culerrier, A. Barre, A. Didier, and P. Rouge. *Plant Physiology and Biochemistry*, 2006, 44(10):535-542.
30. Dillon T. M., P. V. Bondarenko, D. S. Rehder, G. D. Pipes, G. R. Kleemann, and M. S. Ricci. *J. Chrom. A,* 2006, 1120:112-120.
31. Iavarone A. T., J. C. Jurchen, and E. R. Williams. *Anal. Chem.* 2001, 73:1455-1460.
32. Sossountzov L., L. Ruiz-Avila, F. Vignols, A. Jolliot, V. A. F. Tchang, M. Grosbois, F. Guerbette, E. Miginiac, M. Delseny, P. Puigdomenech, and J.-C. Kader. *The Plant Cell*, 1991, 3:923-933.

What is claimed is:

1. A method of determining the allergen content of a composition, the method comprising:
   providing a composition comprising an allergen;
   at least partially purifying the allergen from the composition to form an extract;
   placing the extract in a sampling container comprising polypropylene vial or polypropylene vial insert, and adding bovine serum albumin to the extract to minimize adsorption of the allergen in the extract to the sampling container; and
   determining the amount of allergen in the extract contained in the sample container using liquid chromatography with ultraviolet and/or mass spectrometric detection.

2. The method according to claim 1, wherein the liquid chromatography is two-dimensional liquid chromatography.

3. The method according to claim 1, wherein the allergen is a food allergen, latex allergen, and/or an aero-allergen.

4. The method according to claim 3, wherein the food allergen is a food cereal crop, peanut, tree nut, milk, egg, crustacean, fish, or potato allergen.

5. The method according to claim 4, wherein the food cereal crop allergen is maize lipid transfer protein.

6. The method according to claim 3, wherein the aero-allergen is a pollen or a spore.

7. A method of determining an amount of lipid transfer protein allergen in maize kernel, the method comprising:
   extracting a maize-derived lipid transfer protein (LTP) allergen having a molecular mass of 9 kDa from ground maize kernel to form an extract;
   determining the amount of the maize-derived LTP allergen in the extract using liquid chromatography with ultraviolet and/or mass spectrometric detection.

8. The method according to claim 7, wherein the liquid chromatography is two-dimensional liquid chromatography.

9. The method according to claim 1, wherein adding bovine serum albumin to the extract comprises adding bovine serum albumin at a concentration of 0.3 mg/mL.

10. A method of determining the allergen content of a composition, the method comprising:
- providing a composition comprising multiple isoforms or variants of an allergen;
- at least partially purifying the allergen from the composition to form an extract; and
- determining the amount of allergen in the extract using liquid chromatography with ultraviolet and/or mass spectrometric detection, wherein the liquid chromatography is performed using a column packed with particles having 1.7 μM in size;
- wherein the allergen is maize lipid transfer protein.

11. The method according to claim 10, wherein determining the amount of allergen in the extract using liquid chromatography with ultraviolet and mass spectrometric detection comprises determining the amounts of one or more variants or isoforms of the allergen with ultraviolet and mass spectrometric detection.

12. The method according to claim 10, wherein the liquid chromatography is two-dimensional liquid chromatography.

* * * * *